United States Patent

Fuchs et al.

[11] Patent Number: 6,016,202
[45] Date of Patent: Jan. 18, 2000

[54] METHOD AND APPARATUS FOR MEASURING MATERIAL PROPERTIES USING TRANSIENT-GRATING SPECTROSCOPY

[75] Inventors: Martin Fuchs, Uxbridge, Mass.; John A. Rogers, Castle Rock, Colo.; Matthew J. Banet, Cambridge, Mass.

[73] Assignee: U.S. Philips Corporation, New York, N.Y.

[21] Appl. No.: 08/885,555

[22] Filed: Jun. 30, 1997

[51] Int. Cl.[7] .................................................. G01B 9/02

[52] U.S. Cl. ...................................... 356/432 T; 356/359

[58] Field of Search ................................ 356/432, 432 T, 356/359, 360

[56] References Cited

U.S. PATENT DOCUMENTS

| | | |
|---|---|---|
| 3,462,223 | 8/1969 | Tiemann et al. . |
| 4,522,510 | 6/1985 | Rosencwaig et al. . |
| 4,655,547 | 4/1987 | Heritage et al. . |
| 4,710,030 | 12/1987 | Tauc et al. . |
| 4,728,165 | 3/1988 | Powell . |
| 4,812,036 | 3/1989 | Inoue . |
| 4,939,368 | 7/1990 | Brown . |
| 5,062,693 | 11/1991 | Beratan et al. . |
| 5,132,824 | 7/1992 | Patel et al. . |
| 5,220,403 | 6/1993 | Batchelder et al. . |
| 5,263,039 | 11/1993 | Skupsky et al. . |
| 5,285,438 | 2/1994 | Marchand et al. . |
| 5,344,236 | 9/1994 | Fishman . |
| 5,361,638 | 11/1994 | Pettersson et al. . |
| 5,438,879 | 8/1995 | Reda . |
| 5,479,256 | 12/1995 | Tamai et al. . |
| 5,546,811 | 8/1996 | Rogers et al. . |
| 5,633,711 | 5/1997 | Nelson et al. ................. 356/432 |
| 5,672,830 | 9/1997 | Rogers et al. . |
| 5,734,470 | 3/1998 | Rogers et al. . |

OTHER PUBLICATIONS

Allen et al., "Microfabricated Structures for the in situ Measurement of Residual Stress, Young's Modulus, and Ultimate Strain of Thin Films", Appl. Phys. Lett., 51:241–243, 1987.

Bauer et al., "Determination of the Stresses and Properties of Polymer Coatings", J. of Coatings Technology, 60:51–55, 1988.

Coburn et al., "Stress in Polyimide Coatings", J. of Polymer Science: Part B: Polymer Physics, 32:1271–1283, 1994.

Duggal et al., "Resolution of Conflicting Descriptions of Propylene Glycol Relaxation Dynamics Through Impulsive Stimulated Scattering Experiments", Polymer Communications, 32:356–360, 1991.

Duggal et al., "Real–Time Optical Characterization of Surface Acoustic Modes of Polymide Thin–Film Coatings", J. Appl. Phys. 72:2823–2839, 1992.

Fishman et al., "Surface Selectivity in Holographic Transient Grating–Diffraction", Stanford University, Stanford, CA; W.W. Hansen Exp. Phys. Lab. & Dept. of Chemistry.

(List continued on next page.)

*Primary Examiner*—Robert H. Kim
*Attorney, Agent, or Firm*—Anne E. Barschall

[57] ABSTRACT

The invention provides an apparatus for measuring a property of a sample (using, e.g., ISTS) that includes: 1) an excitation laser that generates an excitation laser beam; 2) an optical system aligned along an optical axis that separates the excitation laser beam into at least three sub-beams; 3) an imaging system aligned along the optical axis that collects the sub-beams and focuses them onto the sample to form an optical interference pattern that generates a time-dependent response in the sample; 4) a probe laser that generates a probe laser beam that diffracts off the time-dependent response to form a signal beam; 5) a detector that detects the signal beam and in response generates a radiation-induced electronic response; and 6) a processor that processes the radiation-induced electronic response to determine the property of the sample.

32 Claims, 7 Drawing Sheets

OTHER PUBLICATIONS

Goldsmith et al., "Measurement of Stresses Generated to Cured Polyimide Films", J. Vac. Sci. Technol. 1:407–409, 1983.

Head et al., "Determination of Shear Stress at a Solder Paste/Stencil Interface", Mat. Res. Soc. Symp. Proc. 323:425–433, 1994.

Maden et al., "Stress Analysis of Thin Polyimide Films Using Holographic Interferometry", Experimental Mechanics 31:179–184, 1991.

Rogers et al., "Study of Lamb Acoustic Waveguide Modes in Unsupported Polyimide Thin Films Using Real–Time Impulsive Stimulated Thermal Scattering", J. Appl. Phys. 75:1534–1556, 1994.

Duggal, "Picosecond–Microsecond Structural Relaxation Dynamics in Polypropelyne Glycol", Journal of Chemical Physics, No. 94, pp. 7677–7688, Jun. 15, 1991.

Rogers et al., "Real–Time In Situ Characterization of Thin Films", Chemf. 8, 27 (1992), pp. 4–8.

Whitman et al., Appl. Optics, 8, 1567 (1969).

Nizzoli et al., Dynamical Properties of Solids (ed. G.K. Horton et al., North–Hollandn Amsterdam, 1990) vol. 6, 283.

Bortolani et al., J. Phys. C., 16, 1757 (1983).

Fishman I.M. et al., "Surface Selectivity in Four–Wave Mixing: Transient Gratings as a Theoretical and Experimental Example", J. Opt. Soc. Am. B., vol. 8, No. 9, Sep. 1991, pp. 1880–1888.

Barish et al., "Photoinduced Ionization of Bovine Serum Albumin by Holographic Relaxation Methods", J. Chem. Phys. 85:4194–4195, 1986.

Burzynski et al., "Study of Anisotrophy of Acoustic Wave Propagation in Stretched poly(vinylidene difluoride) Film Using the Picosecond Transient Grating Technique", Polymer, 30:1247–1250, 1989.

Deeg et al., "New Grating Experiments in the Study of Irreversible Photochemical Reactions", IEEE J. Quantum Electronics, QE–22:1476–1481, 1986.

Espinet et al., "Laser–induced Gratings in Nematic/Cholesteric Mixtures", App. Phys. Letters, 50:1924–1926, 1987.

Greene et al., "Picosecond Relaxation Dynamics in Polydiacetylene–pTs", Chem. Phys. Letters, 139:381–385, 1987.

Meth et al., "Experimental and Theoretical Analysis of Transient Grating Generation and Detection of Acoustic Waveguide Modes in Ultrathin Solids", J. App. Phys. 67:3362–3377, 1990.

Meth et al., "Generation and Detection of Acoustic Waveguide Modes in Ultrathin Crystals Using the Transient Grating Technique", Chem. Phys. Letters, 162:306–312, 1989.

Nelson et al., "Optical Generation of Tunable Ultrasonic Waves", J. App. Phys., 53:1144–1149, 1982.

Nizzoli, "Problems with the Determination of Elastic Constants from Higher–Order Surface Waves: Results for Al on NaCl", Physical Review B, 37:1007–1010, 1988.

Noll et al., "Picosecond Photoinduced Index Changes in a Si:H and Related Alloys Measured by Transient Grating Experiments", J. Non–Crystalline Solids, 97 & 98:141–144, 1987.

Portella et al., "Four–Wave Mixing Experiments in Cresyl Violet Thin Films: Inadequacy of a Two–Level Interpretation", J. Phys. Chem., 91:3715–3719, 1987.

Prasad, "Non–Linear Optical Effects in Thin Organic Polymeric Films", Thin Solid Films, 152:275–294, 1987.

Rao et al., "Third Order Nonlinear Optical Interactions in Thin Films by Poly–p–phenylenebenzobisthiazole Polymer Investigated by Picosecond and Subpicosend Degenerate Four Wave Mixing", App. Phys. Letters, 48:1187–1189, 1986.

Rao et al., "Picosecond Transient Grating Studies of Polymeric Thin Films", App. Phys. Letters, 48:387–389, 1986.

Rose et al., "Picosecond Transient Grating Transport in Anthracene Single Crystals, Measurements of Singlet Excitation", Chem. Phys. Letters, 106:13–19, 1984.

Rao et al., "Picosecond Laser–Induced Transient Grating Probe of the Mechanical Properties of High–Modulus Poly(p–phenylenebenzobisoxazole–2.6–diyl)", Macromolecules, 22:985–989, 1989.

Rothenhausler, "Plasmon Surface Polariton Fields for the Characterization of Thin Films", Thin Solid Films, 159:323–330, 1988.

A.R. Duggal et al., "Real–time Characterization of Acoustic Modes of Polyimide Thin–Film Coatings Using Impulsive Stimulated Thermal Scattering", App. Phys. Lett., 60(6) Feb. 10, 1992, pp. 692–694.

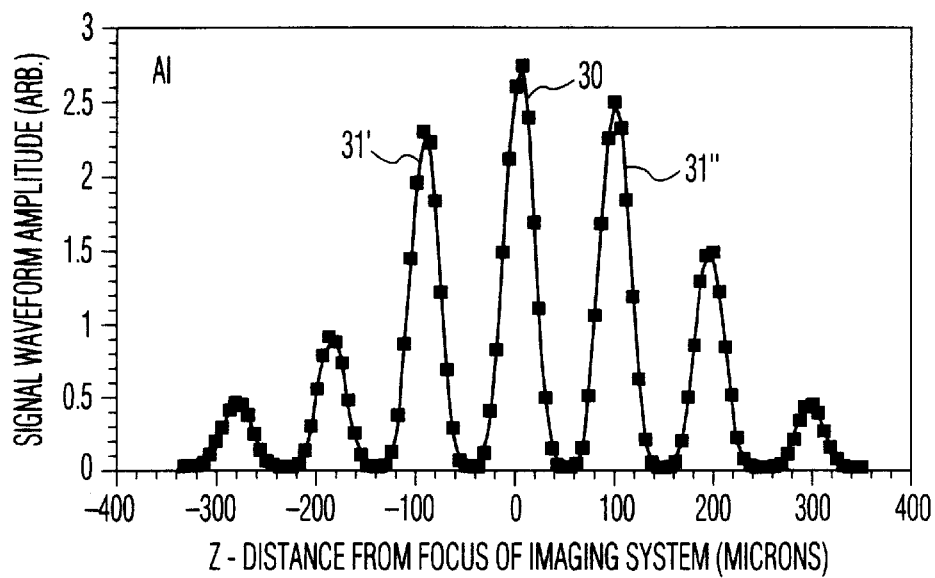
FIG. 5
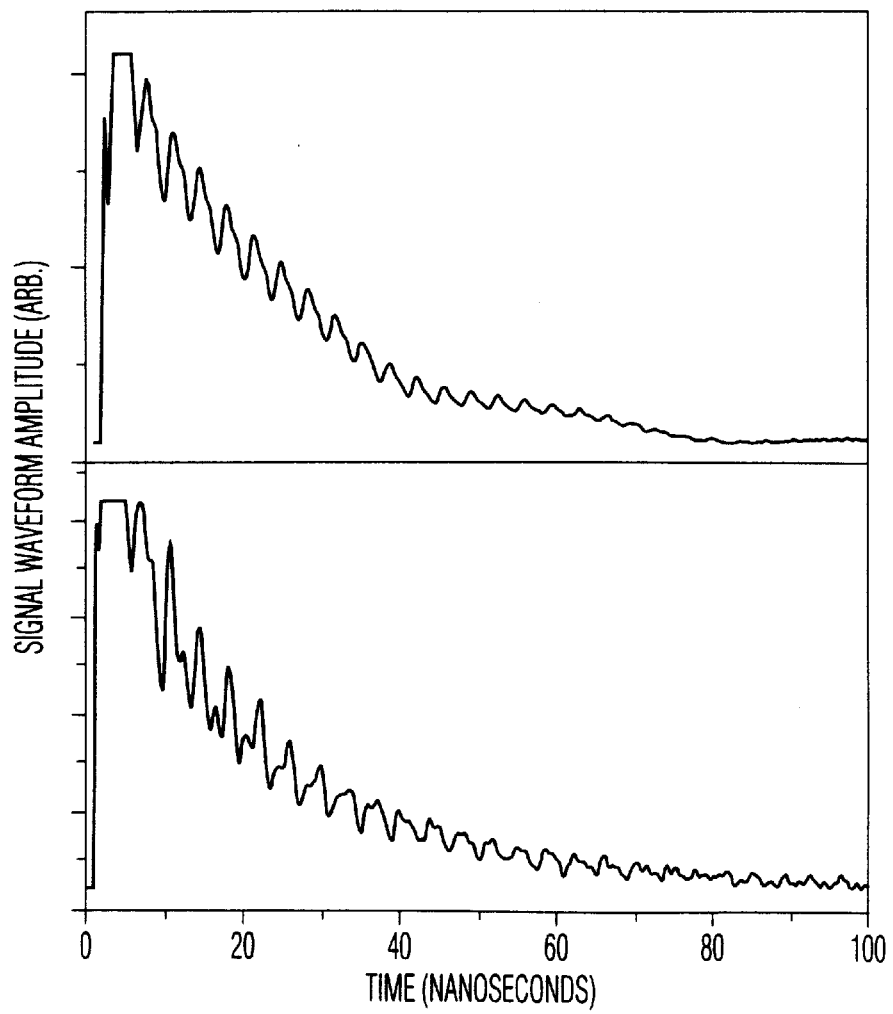
FIG. 6A
FIG. 6B

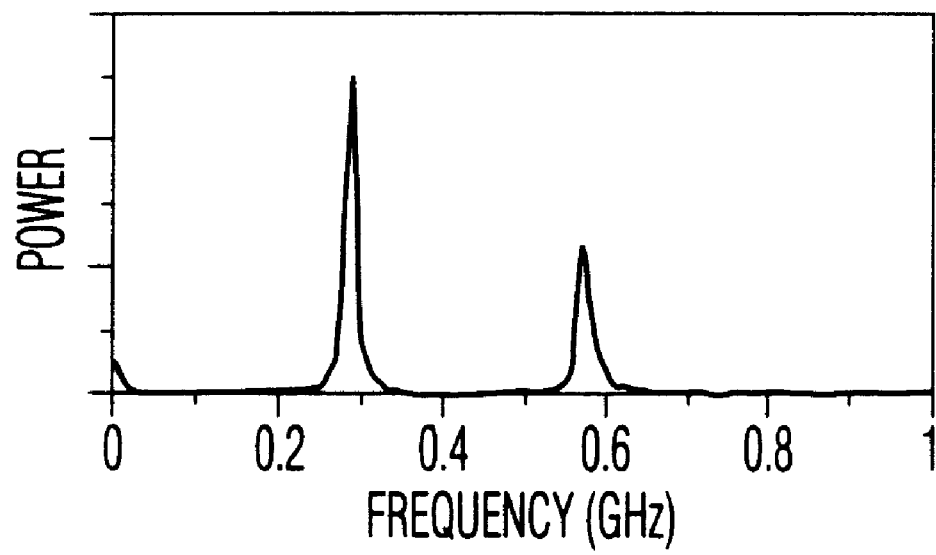
FIG. 6A1
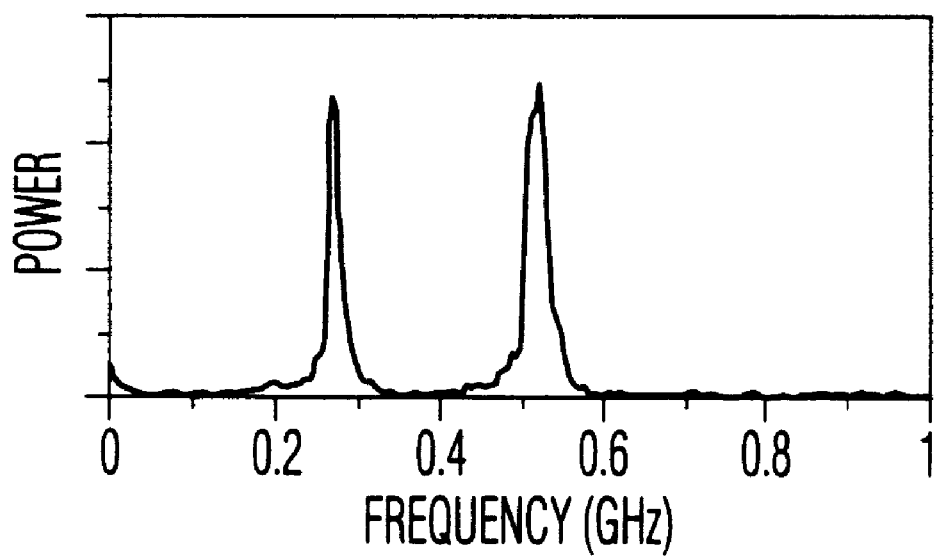
FIG. 6B1

METHOD AND APPARATUS FOR MEASURING MATERIAL PROPERTIES USING TRANSIENT-GRATING SPECTROSCOPY

BACKGROUND

This invention relates to optical systems for measuring properties of a sample, e.g., the thickness of a thin film.

An optical measurement called four-wave mixing (FWM) has been used previously to measure a variety of different material properties, such as film thickness, and film delamination. In FWM measurements, two excitation laser beams are overlapped in time and space on a sample s surface to form a spatially varying optical interference pattern. The pattern consists of alternating "light" (i.e., constructive interference) and "dark" (i.e., destructive interference) regions; the spacing between these regions depends on the wavelength of the laser beams and the angle therebetween. In a class of FWM measurements called impulsive stimulated thermal scattering (ISTS), the excitation laser beam contains a series of short (e.g., a few hundred picoseconds) optical pulses. These pulses of radiation are absorbed by the sample in the light regions, but not in the dark regions, to excite a "transient grating". This process heats and thermally expands the irradiated regions to launch coherent, counter-propagating acoustic waves whose wavelength and direction match those of the interference pattern. When ISTS is used to measure strongly absorbing-films (e.g., metal films), the acoustic waves generate a time-dependent "ripple" on the film's surface that oscillates at the acoustic frequency. A probe beam then diffracts off the transient grating to form a series of signal beams, each of which represents a different diffracted order (e.g, the +/−1 and +/−2 orders). The signal beams oscillate in intensity at the acoustic frequency. One of the signal beams is detected and monitored to measure the properties of the sample.

Use of ISTS to measure film thickness and a variety of other properties is described, for example, in U.S. Pat. No. 5,633,711 (entitled MEASUREMENT OF MATERIAL PROPERTIES WITH OPTICALLY INDUCED PHONONS), U.S. Ser. No. 08/377,308 (entitled OPTICAL MEASUREMENT OF STRESS IN THIN FILM SAMPLES, filed Jan. 24, 1995), U.S. Ser. No. 08/783,046 (entitled METHOD AND DEVICE FOR MEASURING FILM THICKNESS, filed Jul. 15, 1996), and U.S. Ser. No. 08/855,786 (entitled METHOD AND APPARATUS FOR MEASURING THE CONCENTRATION OF IONS IMPLANTED IN SEMICONDUCTING MATERIALS, filed concurrently herewith), the contents of which are incorporated herein by reference.

There are several optical systems that generate the two excitation beams needed for ISTS. In a typical measurement, for example, a single excitation beam passes through a beam-splitter to form two excitation beams of roughly equal intensity. An imaging system (e.g., a lens) then collects these beams and then spatially overlaps them on the sample to form an optical interference pattern that includes the light and dark regions described above.

While useful for many types of FWM experiments, beam-delivery systems that generate two excitation beams, such as those using beam-splitters, suffer drawbacks. For example, these systems often have a relatively long depth of focus, i.e., the beams are overlapped for a relatively long distance. This makes it difficult to position the sample in the exact image plane of the imaging system. Another disadvantage is that the diffraction efficiency of the transient grating formed by two excitation beams is often quite small (e.g., on the order of $10^{-4}$–$10^{-5}$). This means that the diffracted signal beam is often weak and difficult to measure. A weak signal beam, in turn, makes it difficult to precisely measure the acoustic frequency and any corresponding property (e.g., film thickness).

SUMMARY

The above-mentioned disadvantages are overcome in part using a method and apparatus that include improvements to beam-delivery systems that generate excitation beams for FWM measurements. These improvements are described with respect to several different optical systems.

In one improvement, a beam-delivery system includes a phase mask that generates three beams, rather than two, to form the transient grating in the sample. In a typical embodiment, the three beams are equally spaced in a linear fashion (i.e., the center, right, and left beams) prior to being imaged onto the sample. When focused with an imaging system, the center beam propagates down a central optical axis of the beam-delivery system, while the right and left beams converge toward the same spot at the same angle but on opposite sides of the center beam. The beams are overlapped on the sample so that two different transient gratings are simultaneously formed: (1) a grating is formed by the center beam and each of the right and left beams; and (2) a grating is formed by the right and left beams. The laser beams forming these gratings are separated by different angles (i.e., $\theta$ and $\theta/2$), and thus they have different spatial frequencies and will simultaneously excite acoustic waves having different acoustic frequencies.

In another improvement, the excitation laser beam is collimated prior to irradiating the phase mask that generates the excitation beams. Collimating the beam in this way reduces variations in the distance separating the light and dark regions of the interference pattern. This consequently improves the precision to which the acoustic wave is measured in the sample. In another improvement, multiple diffracted signal beams, rather than just a single beam, are collected and imaged onto the photodetector. This increases the intensity of the measured signal and thus further improves the precision of the measurement.

In one aspect, the invention provides an apparatus for measuring a property (e.g., thickness) of a sample that includes: 1) an excitation laser that generates an excitation laser beam; 2) a beam-delivery system, aligned along an optical axis, that separates the excitation laser beam into at least three sub-beams; 3) an imaging system aligned along the optical axis that collects the sub-beams and focuses them onto the sample to form an optical interference pattern that generates a time-dependent response in the sample; 4) a probe laser that generates a probe laser beam oriented to diffract off the time-dependent response to form at least one signal beam; 5) a detector that detects at least one signal beam (and in some cases, two signal beams) and in response generates a radiation-induced electronic response; and 6) a processor that processes the radiation-induced electronic response to determine the property of the sample.

In a typical embodiment, the three sub-beams are generated with a transmissive phase mask, and one of the sub-beams propagates along the optical axis of the optical system. For example, the phase mask may contain a pattern that is oriented along the optical axis and partially diffracts the excitation laser beam to form at least two of the sub-beams, and partially transmits the excitation laser beam to form the remaining sub-beam. In this case, the sub-beam transmitted by the pattern is oriented along the optical axis of the optical system, and the diffracted sub-beams are oriented on each side of the transmitted sub-beam. Each of the sub-beams diffracted by the pattern has a roughly equal intensity that is typically between 20% and 40% of the excitation laser beam, and the sub-beam transmitted by the pattern has an intensity that is between 20% and 60% of the excitation laser beam.

In other embodiments, the interference pattern contains interference fringes separated by a distance of between 3 and 20 microns. Such an interference pattern is generated with a phase mask that contains multiple patterns, each of which generates sub-beams that diverge from the phase mask at a different angle.

In another aspect, an apparatus includes: 1) an excitation laser that generates an excitation laser beam; 2) a beam-delivery system, aligned along an optical axis, that separates the excitation laser beam into at: least two sub-beams; 3) an imaging system aligned along the optical axis that collects the two sub-beams and focuses them onto the sample to form an optical interference pattern that generates a time-dependent response in the sample; 4) a probe laser that generates a probe laser beam oriented to diffract off the time-dependent response to form at least two signal beams; 5) an optic oriented in the optical axis that transmits the excitation sub-beams, reflects the probe beam towards the sample, and reflects at least one signal beam; 6) a detector that detects at least one signal beam and in response generates a radiation-induced electronic response; and 7) a processor that processes the radiation-induced electronic response to determine the property of the sample. In a typical embodiment, the optic is a beam-splitter oriented to reflect at least two signal beams toward the photodetector.

The apparatus described above measures a property of a sample, such as film thickness, film delamination, thermal diffusivity, elastic moduli, loss moduli, and concentration of implanted ions. These properties can be measured from a wide range of samples, e.g., metal thin films, semiconductor films, semiconductor substrates, and polymeric materials. In another aspect, the apparatus accurately positions a sample along an optical axis. In this case, for example, the apparatus generates a data set by measuring data at a number of positions along the optical axis, and then processes the data set to position the sample along the optical axis. In one case, the processing step includes fitting the data set with a function, e.g., a Gaussian or Lorentzian function or a derivative or analog thereof.

The improved optical systems described above reduces measurement errors and increases signal strengths when compared to existing systems used in FWM measurements. For example, the three-beam system has a relatively sharp effective depth of focus (i.e., depth of field), making it possible to position a sample precisely in the image plane of the imaging system. This minimizes errors in the measurement that are associated with incorrectly positioning the sample along the focus. Measurement errors caused by incorrect positioning are even further reduced by collimating the excitation beam prior to irradiating the phase mask. In addition, since the three-beam optical system simultaneously excites and measures two acoustic frequencies in a sample, two data points can be collected in the time normally required to collect one data point. This reduces the time required to make ISTS measurements requiring multiple data points.

The system also increases the magnitude of the measured signal waveform. For example, the diffraction efficiency of a transient grating formed with three beams is large relative to that formed with only two beams. This increases the magnitude of each the diffracted signal beams. The signal measured with the photodetector is even further increased by collecting multiple signal beams, rather than just a single beam. These improvements result in better signal-to-noise ratios in the measured data, and thus increase the precision of an ISTS-based measurement.

Still other advantages will be apparent from the following detailed description, and from the claims.

BRIEF DESCRIPTION OF THE DRAWINGS

FIG. 5 is a plot showing the signal waveform amplitude measured from an aluminum film as a function of z using the three-beam optical system;

FIGS. 6A and 6B are time and frequency-domain plots of a signal waveform measured with a three-beam optical system from, respectively, aluminum and ti:nitride films;

DETAILED DESCRIPTION

Figure 1:
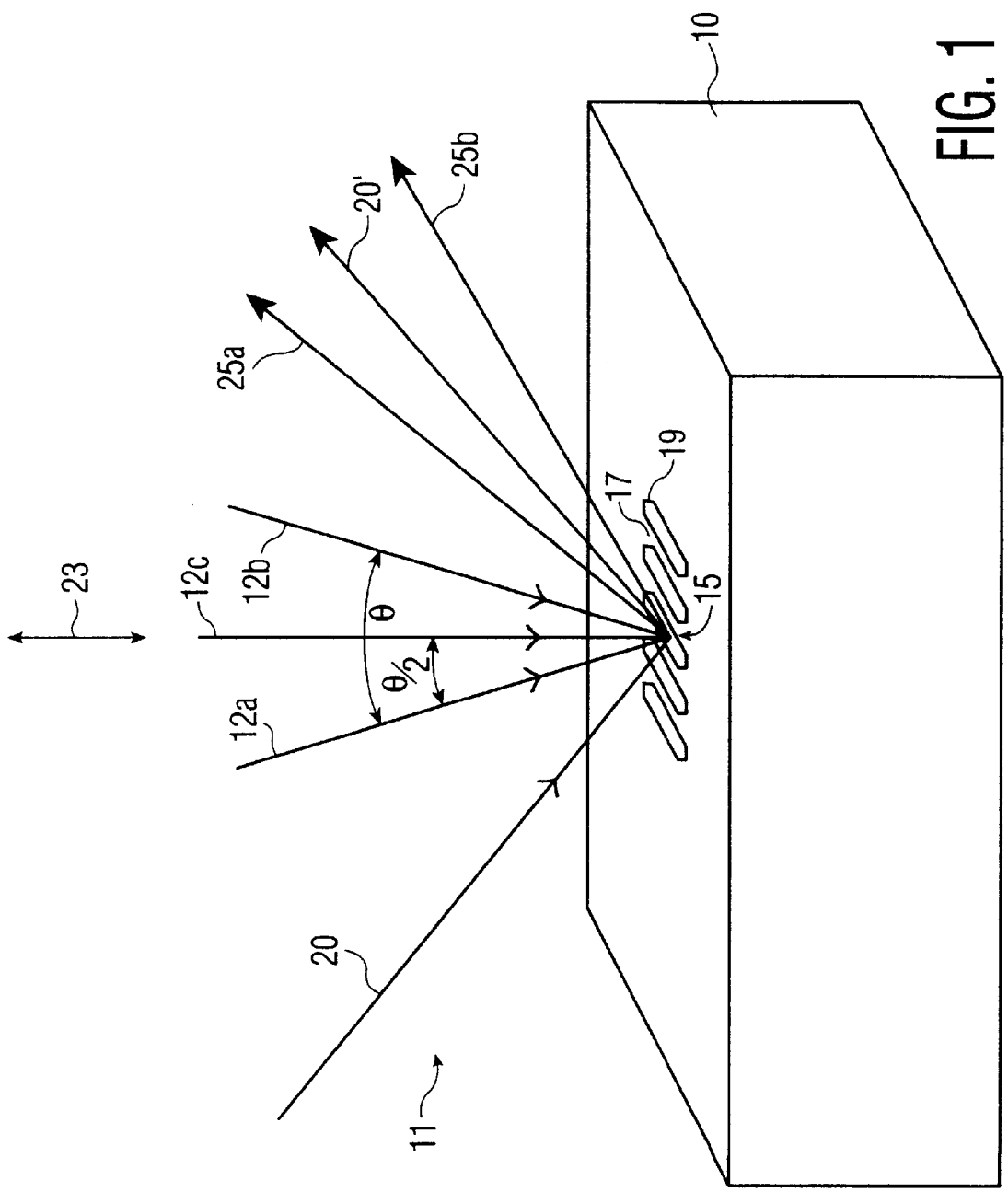
FIG. 1 is a schematic drawing of the excitation, probe, and signal beams used in a three-beam optical system.

FIG. 1 shows a three-beam configuration 11 that measures a property (e.g., film thickness) of a sample 10 using ISTS. In the three-beam configuration 11 three excitation sub-beam beams 12a–c are overlapped in time and space on the sample s surface to generate a transient grating. The three-beam configuration 11 features: (1) a center sub-beam 12c that propagates along an optical axis 23; and (2) left 12a and right 12b sub-beams that converge on the sample s surface at an angle of θ/2 relative to the optical axis. The left 12a and right 12b sub-beams have roughly equal intensity (typically between 20% and 40% of the incident excitation laser beam) that is typically greater than that of the center sub-beam 12c. All sub-beams are separated from an incident laser beam generated from an excitation laser (not shown in the figure). Each beam contains a short laser pulse typically having a duration of a few hundred picoseconds and a wavelength (typically in the infrared or visible spectral regions) that is strongly absorbed by the sample.

Once overlapped, the three optical excitation beams interfere to form a spatially varying interference pattern 15 containing alternating light (constructive interference) 17 and dark (destructive interference) 19 regions. In ISTS, radiation is absorbed strongly by the sample 10 in the light regions 17, but not in the dark regions 19. The absorbed radiation impulsively heats the sample in those regions during the short duration of the excitation pulse and initiates a time-dependent acoustic response that has been described in detail in the above-mentioned references. This response is measured in its entirety by irradiating sample near or on the interference pattern 15 with a probe pulse 20. The probe pulse 20 (typically several hundred microseconds) is longer than the duration of the time-dependent response, and is partially reflected to form a reflected beam 20, and partially diffracted to form a pair of signal beams 25a, 25b that are the +1 and −1 diffracted orders of the transient grating. Higher diffracted orders (e.g., the +/−2, +/−3 orders) are also formed, but are weaker than the +/−1 orders. At least one of the signal beams is detected with a photodetector (not shown in the figure) to generate a signal waveform. The signal waveform is then analyzed to measure a property of the sample.

In ISTS the three sub-beams 12a–c are focused onto the sample with an imaging system that overlaps them in a cylinder-shaped volume having a long axis (called the Raleigh length ) that increases with the focal length of the imaging system and the wavelength of the sub-beams. The magnitude of the Raleigh length determines the sharpness of the imaging system s focus: a relatively short Raleigh length indicates a sharp focus. Only when the sample is positioned along the Raleigh length will the sub-beams be overlapped to form a transient grating on its surface. Thus, a signal waveform is only measured when the sample is positioned along the Raleigh length.

Within the Raleigh length the spatial periodicity (i.e., the distance between the light and dark regions) of the interference pattern can vary slightly, causing changes in the frequency of the excited acoustic wave. Since many properties of the sample can be calculated from this frequency, such a variation can result in an erroneous measurement, even when the sample appears to be properly positioned. It is therefore desirable to have a beam-delivery system that: 1) generates beams that are sharply focused over a short Raleigh length; and 2) minimizes the dependence of frequency on the sample s position within the Raleigh length.

Figure 2:
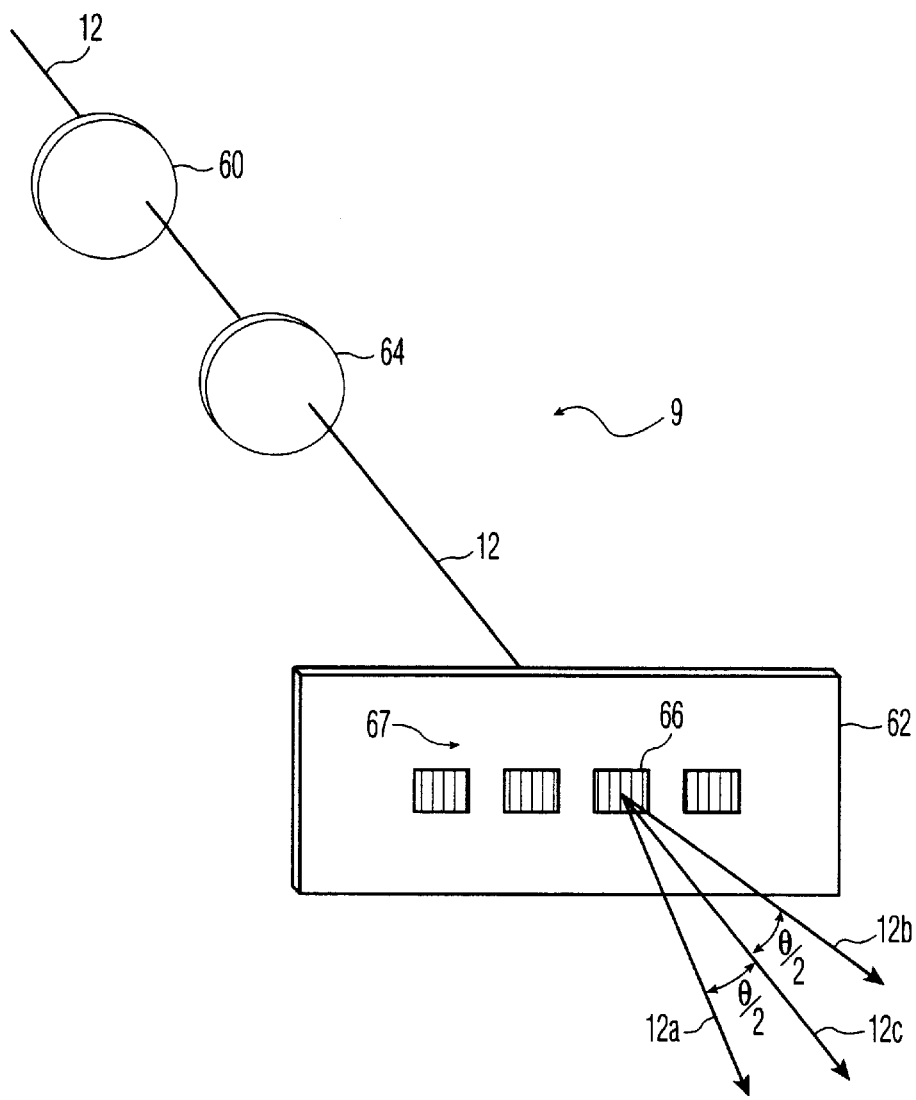
FIG. 2 is a front view of a beam-delivery system that includes a phase mask that diffracts an incident excitation laser beam to form three sub-beams.

FIG. 2 shows beam-delivery system 9 that realizes both of these improvements. The system 9 includes a phase mask 62 containing a diffracting pattern 66 that generates the excitation sub-beams 12a–c. Here, an incident optical excitation beam 12 is focused along the x axis onto the pattern 66 using a cylindrical lens 64. The beam 12 is well collimated along the y axis using a collimating lens 60. The pattern partially diffracts the incident beam into the +1 and −1 orders (to form the left 12a and right 12b sub-beams) and partially transmits the incident beam 12 to generate the center sub-beam 12c. Higher diffracted orders are generated by the phase mask, but are typically spatially filtered before impinging the sample. These orders are therefore not shown in the figure. The diffracted sub-beams emerge along the x axis at an angle θ/2 relative to the transmitted sub-beam. This angle depends on the periodicity of the irradiated pattern 66 (described in more detail below), and will determine the periodicity of the interference pattern used to excite the sample. These sub-beams are then collected and focused onto the sample to form an optical interference pattern that is an image of the irradiated pattern 66. A related process is described in U.S. Ser. No. 08/377,310 (entitled SIMPLIFIED DEVICE AND METHOD FOR TIME-RESOLVED OPTICAL MEASUREMENTS, filed Jan. 24, 1997) the contents of which are incorporated herein by reference. A phase mask typically contains multiple patterns 67, each of which diffracts sub-beams at a different angle and thus forms a different interference pattern on the sample.

Phase masks that produce three beams from a single impinging beam are made using techniques well known in the optical arts. For example, the diffraction pattern 66 is typically an alternating series of grooves etched into a glass substrate. The depth of the grooves relative to the wavelength of the incident radiation determines how much radiation is diffracted into to sub-beams, while the periodicity of the grooves determines the angle at which the sub-beams emerge from the pattern. To achieve the three-beam configuration, the depth of the grooves is chosen to be slightly less than optimal so that some of the incident radiation passes directly through the mask, rather than being diffracted into the non-zeroth orders.

Figure 3:
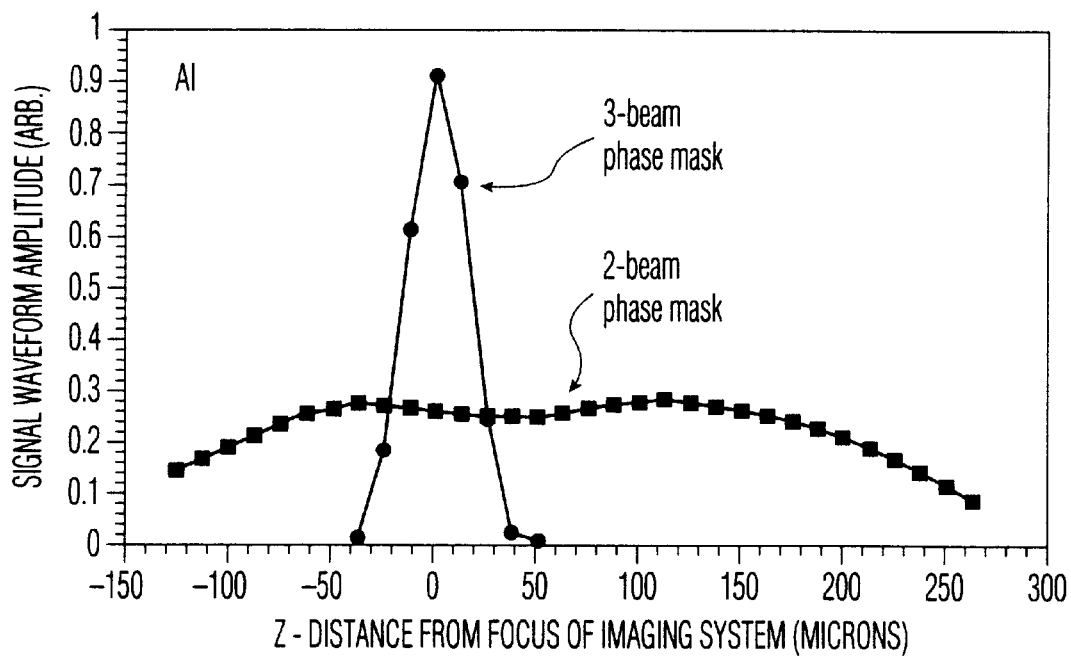
FIG. 3 is a plot of the signal waveform amplitude measured from an aluminum film as a function of the distance the sample is placed from the focus of an imaging system (z) for the two-beam and three-beam optical systems.
Figure 4:
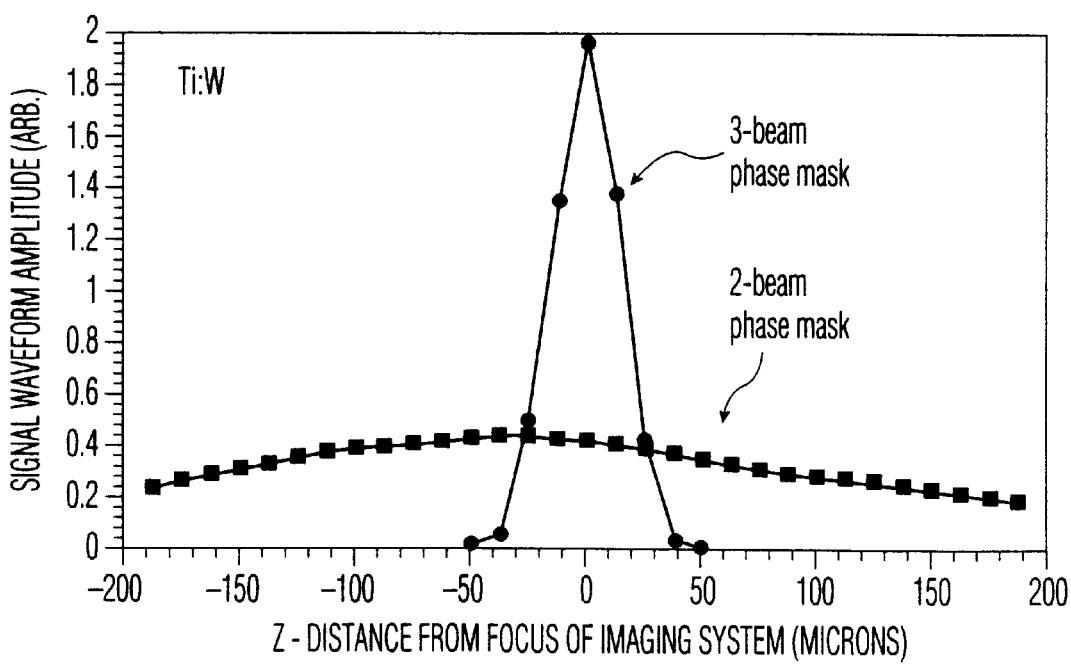
FIG. 4 is a plot of the signal waveform amplitude measured from a ti:tungsten film as a function of z for the two-beam and three-beam optical systems.

FIGS. 3 and 4 illustrate how the effective focus of the three-beam configuration is significantly sharper than that of the two-beam configuration. These figures plot the amplitude of a diffracted signal waveform as a function of the position of a sample from the image plane of the imaging system (z) for both the two-beam and three-beam configurations. The image plane of the imaging system occurs at z=0.

The figures show, respectively, data measured from aluminum and ti:tungsten, two films commonly used in the microelectronics industry. The data show ES relatively strong dependence of the signal magnitude on z for the three-beam configuration, indicating the relatively sharp focus of this configuration. For example, for both aluminum and ti:tungsten the full-width, half-maximum (FWHM) of the peak was about 50 microns. Conversely, in both FIGS. 3 and 4, the magnitude of the signal generated in the two-beam configuration has a relatively weak dependence on z: the FWHM is greater than 300 microns. In fact, in FIG. 3, the dependence of the signal waveform amplitude on z is bi-modal, making it even more difficult to determine the exact position of the image plane of the two-beam configuration.

In addition to showing a sharpening of effective focus, FIGS. 3 and 4 indicate how the overall magnitude of the diffracted signal is larger in the three-beam configuration than in the two-beam configuration. For example, in FIG. 3 the maximum signal waveform amplitude for the three-beam configuration is roughly 3 times that measured using the two-beam configuration. In FIG. 4, the signal waveform amplitude is increased by nearly a factor of 5 for the three-beam configuration. The measurements for the two configurations were carefully monitored to ensure that factors that might otherwise affect the signal amplitude, such as laser pulse energy and acoustic wavelength, were identical.

FIG. 5 shows the signal waveform amplitude for the three-beam configuration plotted as a function of z along the entire Raleigh length of the imaging system. Several peaks are evident in the data, with the center peak 30 having the largest amplitude, and the side peaks 31, 31 decreasing in amplitude in a symmetrical fashion. Mathematically, this distribution of intensity (D(x,z), where x and z are the axes described in FIG. 2) is described by equation (1), below:

$$D(x,z)=I_0+2I_{+/-1}[(1+\cos(2kx \sin (\theta/2)))-4/\pi\sin(\phi_0) \cos(kx \sin(\theta/2)) \sin(kz(\cos(\theta/2)-1))] \quad (1)$$

where $I_0$ is the intensity of the zeroth order beam, $I_{+/-1}$ is the intensity of the right and left sub-beams, $k=2\pi/\lambda$, where $\lambda$ is the wavelength of the excitation beam, $\theta/2$ is the angle between the right and left sub-beams and the optical axis, and $\phi_0$ is the phase shift associated with the phase mask (typically $\pi/1.3$ for a phase mask that generates three beams, and $\pi$ for a phase mask that generates two beams). Equation 1 neglects the Gaussian envelope that describes the intensity distribution of most laser beams; this effect can be included simply be multiplying the equation by a Gaussian function.

Eqn. 1 indicates that the spatial frequency f D(x,z) is proportional to:

$$f \sim 2k(\sin(\theta/4))^2 \qquad (2)$$

Thus, the effective focus of the imaging system is sharpened by decreasing this frequency, i.e., increasing the angle of the diffracted sub-beams. This is done by increasing the periodicity of the grooves in the diffracting mask.

Eqn. 1 also predicts the increase in diffraction efficiency (shown in FIGS. 3 and 4) observed in the three-beam configuration (where $\phi_0=\pi/1.3$) relative to the two-beam configuration ($\phi_0=\pi$). In the three-beam configuration D(x,z) is maximized at a slight distance (typically a few microns) away from the image plane (z=0). The value of D(x,z) at this position is nearly 50% larger than the maximum value of D(x,z) for the two-beam configuration that occurs at the image plane.

Once generated, data like that shown in FIG. 5 can be fit to determine where to properly position the sample. In one embodiment, the central peak in the data (30 in FIG. 5) is determined and then fit to a Gaussian function. The z value that gives the best fit indicates the optimal location for the sample, i.e., the position that maximizes the diffraction efficiency of the grating pattern.

The three-beam mask can also be used to increase the rate of data collection. A transient grating formed by overlapping two laser beams will have a periodicity T of $$T=\lambda\sin^{-1}(\theta/4) \qquad (3)$$

where $\lambda$ is the wavelength of the excitation radiation and $\theta$ is the angle between the beams forming the grating. As described above, in the three-beam configuration a transient grating is formed from interference between the center sub-beam and each of the right and left sub-beams, and from interference between the right and left sub-beams. Thus, two different gratings (formed by beams separated by $\theta$ and $\theta/2$) are simultaneously formed. This results in simultaneous excitation of two different acoustic frequencies. FIGS. 6A and 6B illustrate this point, showing signal waveforms plotted in the time and frequency domains measured using ISTS in the three-beam configuration. The data were collected from aluminum (FIG. 6A) and ti:nitride (FIG. 62) films, and clearly show the presence of two acoustic frequencies that are measured in the same time period normally required to measure a single acoustic frequency. Measuring two frequencies simultaneously in this way has several advantages. In general, each frequency can be analyzed to determine a property (e.g., film thickness) of the sample being measured; analyzing two frequencies therefore increases the accuracy to which the property is determined. In measurements where multiple frequencies need to be measured from a sample to determine a property (e.g., an acoustic dispersion), simultaneous measurement of two frequencies significantly expedites the measurement process.

Figure 7:
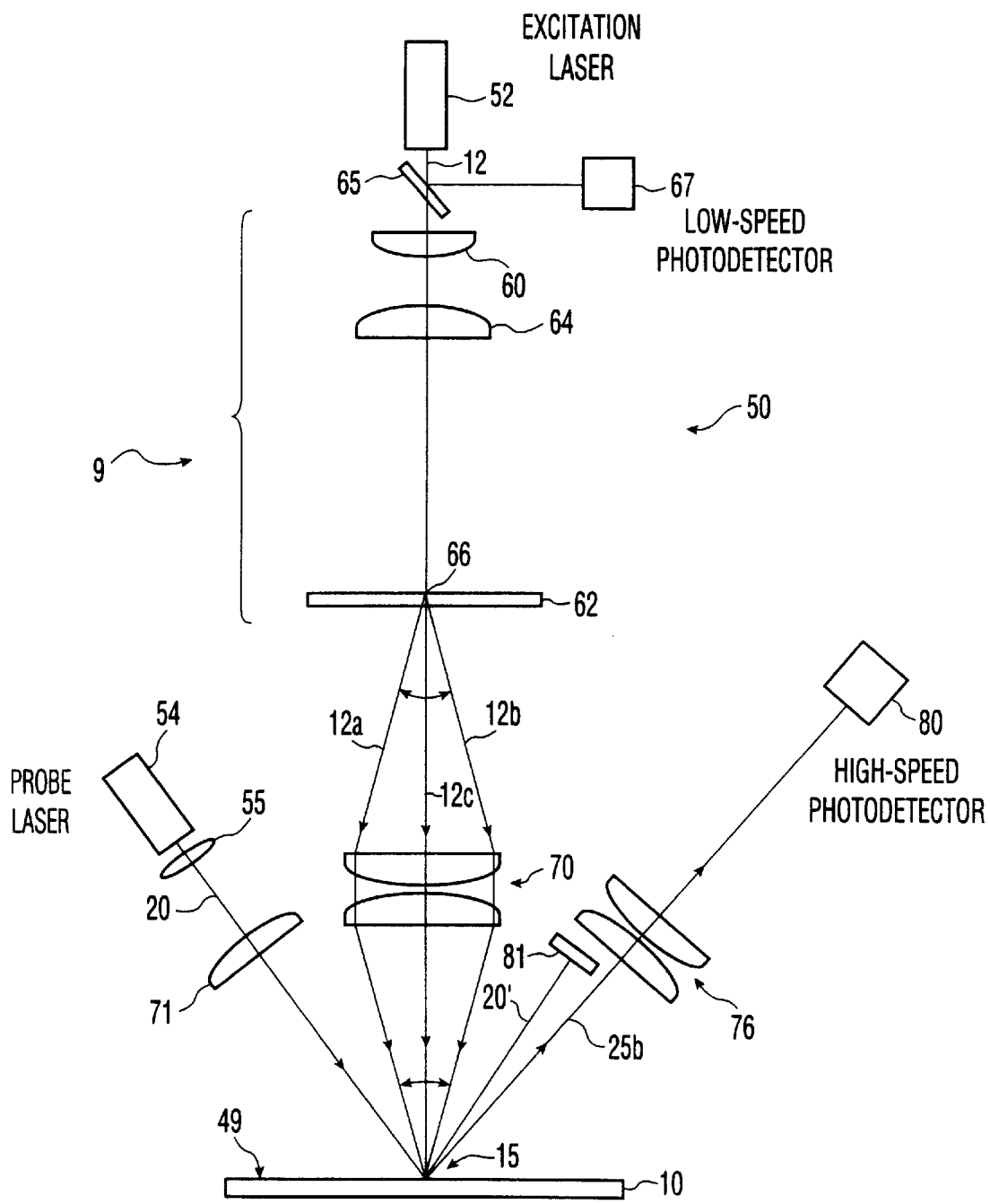
FIG. 7 is a schematic drawing of a three-beam optical system for measuring a property of a sample with ISTS.

FIG. 7 shows an optical system 50 that uses the three-beam configuration to measure the properties of a sample 10 using ISTS. A similar system for making these measurements is described in SIMPLIFIED DEVICE AND METHOD FOR TIME-RESOLVED OPTICAL MEASUREMENTS (U.S. Ser. No. 08/377,310, filed Jan. 24, 1995).

The system 50 includes an excitation laser 52 that generates sub-nanosecond optical pulses that initiate the time-dependent responses in the sample 10, and a probe laser 54 that measures these responses. The excitation laser, for example, can be a Q-switched Nd:YAG laser such as that described in U.S. Pat. No. 5,393,413. The probe laser, for example, can be a modulated diode laser.

The excitation laser 52 generates a beam 12 that is separated into three sub-beams 12a–c with a beam-delivery system 9. The beam-delivery system 9 includes a first collimating lens 60 that collimates the beam 12, and a cylindrical lens 64 that focuses the beam along one axis onto a phase mask 62. A portion of the beam 12 is reflected by a glass cover slip 65 and detected with a low-speed photodetector 67 that generates an electrical pulse for triggering a data-acquisition system (not shown in the figure). The phase mask includes a series of patterns 66, each of which generates a different interference pattern 15 on the sample 10. After impinging a pattern 66 on the phase mask 62, the excitation beam 12 is partially diffracted into sub-beams 12a, 12b, and partially transmitted to form sub-beam 12c. Higher diffracted orders are typically generated by the phase mask and are spatially filtered using a beam block (not shown in the figure). Sub-beams 12a, 12b diverge at an angle $\theta/2$ relative to sub-beam 12c, which is transmitted along an optical axis 23 of the system. The angle of divergence of the diffracted sub-beams 12a,b determines the periodicity of the interference pattern as described in equation 1, above.

A first imaging lens pair 70 collects the three sub-beams 12a–c and focuses and overlaps them onto the surface 49 of the sample 10 to form the interference pattern 15. Absorption of the pattern 68 initiates an acoustic wave through ISTS. Different grating patterns are formed on the sample simply by translating the phase mask 62 so that a new pattern is irradiated with the incident excitation beam 12.

The probe laser 54 generates a probe pulse 20 that is collimated with a second collimating lens 55 and focused onto the interference pattern 15 with a second spherical lens 71 to measure the time-dependent response of the sample. As described above, this response diffracts a portion of the probe pulse 20 to form a signal beam 25b. A beam-stop 81 blocks a reflected portion 20 of the probe beam. A second imaging lens 76 collects the signal beam 25b and focuses it onto a high-speed (e.g., 1 GHz) photodetector 80 to generate a signal waveform. The waveform is then analyzed with a computer (not shown in the figure) to determine a property of the sample.

Figure 8:
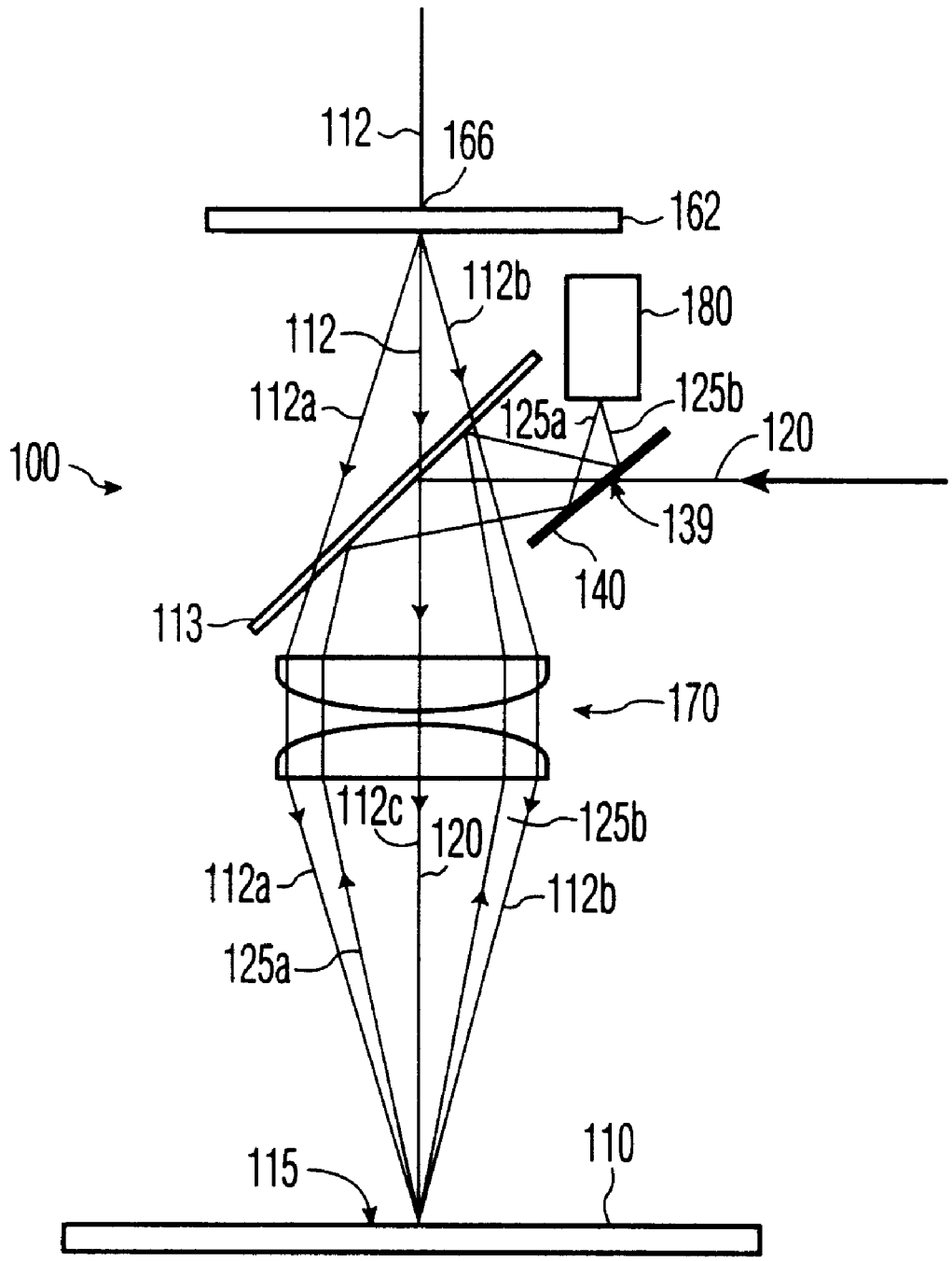
FIG. 8 is a schematic drawing of a modified three-beam optical system for measuring a property of a sample with ISTS.

FIG. 8 shows another optical system 100 for performing ISTS measurements using either the two-beam or three-beam configuration. This system includes fewer optics and occupies less space than the system shown in FIG. 7, and can therefore be used to make measurements in environments that require compact instrumentation. The system 100, for example, could be attached directly to a tool used during fabrication of a microelectronic device, such as a metal-film deposition chamber, to make in situ measurements. These types of measurements are described in more detail in U.S. Ser. No. 08/783,046 (entitled METHOD AND DEVICE FOR MEASURING FILM THICKNESS, filed Jul. 15, 1996).

In a typical embodiment, the system 100 includes a phase mask 162 and pattern 166 that diffracts an incident beam 112 into three sub-beams 112a–c as described above. The sub-beams 112a–c pass through a beam-splitter 113 coated to only reflect a probe laser beam 120. After passing through the beam-splitter 133, a lens pair 170 collects the sub-beams 112a–c and overlaps them onto a sample 110 to form an interference pattern 115 that generates acoustic waves through ISTS as described above.

The acoustic waves are measured with the probe beam 120 that first passes through a clear hole 139 drilled into a mirror 140. The beam-splitter 113 then reflects the probe beam 120 so that it is collinear with the center excitation sub-beam 112c and passes through the lens pair 170, where it is focused onto the interference pattern 115. There, the probe beam 120 is diffracted to form a pair of signal beams 125a,b that propagate back through the lens pair 170 and are reflected by the beam-splitter 113 onto opposite sides of the clear hole 139 drilled into the mirror 140. The mirror reflects both signal beams 125a,b into a photodetector that in response generates a signal waveform that is analyzed as described above.

The optical sources and detection electronics which may be used with the optical systems described above have been described previously in the references described above. Briefly, in order to impulsively generate material motions in a sample (using, e.g., ISTS), the excitation laser beam is pulsed, and may be generated using a light source which is Q-switched, mode-locked, or both. The pulse duration must be short enough to impulsively stimulate material motions in the film. For example, in order to excite acoustic processes, the output pulse typically has a duration of between 100 picoseconds and 1 nanosecond. The energy of the output pulse is typically between 3 and 20 microjoules. In addition, the repetition rate of the pulses must be high enough to allow suitable data averaging (when necessary), but low enough to allow the thermal properties of the sample to recover between laser shots. Typically, the repetition rate is between 1 and 2000 Hz, with the rate being adjusted for measurement of different types of samples. For samples which easily damage, such as thin metal films, it may be desirable to reduce the repetition rate of the excitation laser.

Once excited, the time-dependent properties of the sample are recorded by monitoring the time-dependent diffraction of the probe pulse, which is typically derived from a single-mode laser producing between 0.1 and 1 Watt peak power in the visible or infrared frequency range. The pulse typically has a temporal duration on the order of between 1 and 100 microseconds. Alternatively, a continuous-wave (cw) probe beam can be used.

Light sources other than Nd:YAG lasers may be used to optically excite the film. Suitable lasers include, among others, Nd:YLF, ion (e.g., argon and krypton), Ti:Sapphire, diode, $CO_2$, holmium, excimer, dye, and metal-vapor lasers. Similarly, light sources other than diode lasers may be used as the probe laser. Alternative lasers include ion lasers. Pulsed light sources which may be used to generate the probe beam include Q-switched Nd:YAG, Nd:YLF, Ti:Sapphire, diode, $CO_2$, holmium, excimer, dye, and metal-vapor lasers.

In addition, optical elements other than transmissive phase masks can be used to generate the excitation sub-beams. For example, amplitude masks (i.e., a mask that uses opaque bars rather than transparent grooves to diffract radiation) can be used, as can phase and amplitude and phase masks operating in a reflective mode. In still other embodiments a series of beam-splitters and optical delay lines known in the art can be used to generate the excitation sub-beams.

The samples which may be monitored with the method and apparatus described herein may be bulk (e.g., solids such as metal or semiconductors), thin films (e.g., polymer, semiconductor, or metal films), fluids, surfaces or other samples exhibiting time-dependent material motions. Typical samples include metal films used in the semiconductor industry, such as aluminum, tungsten, titanium, ti:tungsten, ti:nitride, chromium, and cobalt films. The material properties that can be determined in these samples include mechanical, physical (e.g., thickness), elastic, (depth-dependent and/or anisotropic) diffusive, adhesion-based, thermal (e.g., thermal diffusivities) and viscous properties associated with the damping of acoustic waves. In addition, electron relaxation lifetimes, electron-hole recombination times, exciton lifetimes, and bi-exciton lifetimes may additionally be determined in, for example, metal and semiconductor samples.

In bulk systems the dispersion of the acoustic properties allows the frequency dependence of the mechanical (e.g., bulk or shear) modulus to be determined. Additionally, measurement of the thermal diffusion dynamics allows the thermal diffusivity for the acoustic information that is obtained allows determination of the degree of adhesion, delamination properties, and the elastic, shear, and longitudinal moduli, as well as anisotropies in these properties. Depth-dependent properties and residual stresses in thin films can also be determined.

Still other embodiments are within the scope of the following claims.

What is claimed is:

1. An apparatus for measuring a property of a sample, comprising:

an excitation laser that generates an excitation laser beam;

a beam-delivery system, aligned along an optical axis, that separates the excitation laser beam into at least three sub-beams;

an imaging system aligned along the optical axis that collects the at least three sub-beams and focuses them onto the sample to form an optical interference pattern that generates a time-dependent response in the sample;

a probe laser that generates a probe laser beam oriented to diffract off the time-dependent response to form at lest one signal beam;

a detector that detects the at lest one signal beam and in response generates a radiation-induced electronic response; and a processor that processes the radiation-induced electronic response to determine the property of the sample.

2. The apparatus of claim 1, wherein the optical system further contains a transmissive phase mask that generates at least three sub-beams.

3. The apparatus of claim 2, wherein one of the sub-beams propagates along the optical axis of the optical system.

4. The apparatus of claim 3, wherein the phase mask contains a pattern that is oriented along the optical axis and partially diffracts the excitation laser beam to form at least two of the sub-beams, and partially transmits the excitation laser beam to form one of the sub-beams.

5. The apparatus of claim 4, wherein the sub-beam transmitted by the pattern is oriented along the optical axis of the optical system, and the sub-beams diffracted by the pattern are oriented on each side of the sub-beam transmitted by the pattern.

6. The apparatus of claim 4, wherein each of the sub-beams diffracted by the pattern has a roughly equal intensity that is between 20% and 40% of the excitation laser beam, and the sub-beam transmitted by the pattern has an intensity that is between 20% and 60% of the excitation laser beam.

7. The apparatus of claim 1, wherein the interference pattern contains interference fringes separated by a distance of between 3 and 20 microns.

8. The apparatus of claim 1, wherein the phase mask contains multiple patterns, each of which generates sub-beams that diverge from the phase mask at a different angle.

9. The apparatus of claim 1, wherein the property is selected from the group consisting of film thickness, film delamination, thermal diffusivity, elastic moduli, loss moduli, and concentration of implanted ions.

10. The apparatus of claim 1, wherein the detector is oriented to detect at least two signal beams.

11. The apparatus of claim 1 the property of the sample is position of the sample along the optical axis.

12. The apparatus of claim 11, wherein the optical system further contains a transmissive phase mask that generates at least three sub-beams.

13. The apparatus of claim 12, wherein the phase mask contains a pattern that is oriented along the optical axis and partially diffracts the excitation laser beam to form at least two of the sub-beams, and partially transmits the excitation laser beam to form one of the sub-beams.

14. The apparatus of claim 13, wherein the sub-beam transmitted by the pattern is oriented along the optical axis of the optical system, and the sub-beams diffracted by the pattern are oriented along a line on each side of the sub-beam transmitted by the pattern.

15. A sample positioning apparatus comprising:
    the apparatus of claim 11; and
    means to move the sample along the optical axis.

16. The apparatus of claim 15, wherein the processor is configured to processes radiation-induced electrical signals measured at different positions along the optical axis to determine an optimal position along the optical axis to position the sample.

17. A method for determining the property of a sample comprising:
    generating an excitation laser beam;
    separating the excitation laser beam into at least three sub-beams with an optical system comprising an optical axis;
    collecting the at least three sub-beams with an imaging system and focusing them onto the sample to form an optical interference pattern that generates a time-dependent response in the sample;
    diffracting a probe laser beam off the time-dependent response to form a signal beam;
    detecting the signal beam with a detector that in response generates a radiation-induced electrical signal; and
    processing the radiation-induced electrical signal with a processor to determine the property of the sample.

18. The method of claim 17, wherein the generating step comprises passing the excitation laser beam through a phase mask that partially transmits the excitation laser beam to form one of the sub-beams, and partially diffracts the excitation laser beam to form at least two of the sub-beams.

19. The method of claim 17, wherein the property is selected from the group consisting of film thickness, film delamination, thermal diffusivity, elastic moduli, loss moduli, and concentration of implanted ions.

20. A method for positioning a sample along an optical axis of an optical system, comprising the method of claim 17, wherein
    the property is position of the sample along the optical axis;
    the processing step comprises:
        saving the radiation-induced electrical signal in a memory of a computer;
        moving the sample along the optical axis;
        repeating the generating, separating, collecting, diffracting, detecting, and saving steps to generate a data set; and
        further processing the data set with a processor to determine a preferred position along the optical axis at which to position the sample.

21. The method of claim 20, wherein the further processing step comprises fitting the data set with a function.

22. The method of claim 21, wherein the function is a Gaussian or Lorentzian function or a derivative or analog thereof.

23. The apparatus of claim 1 wherein the imaging system overlaps the at least three beams in a cylinder-shaped volume having a long axis that increases with the focal length of the imaging system.

24. The apparatus of claim 1 wherein a focus of the apparatus is significantly sharper than that of a similar apparatus having only two sub-beams.

25. The apparatus of claim 24 wherein the at least one signal beam is stronger than that of a similar apparatus having only two sub-beams.

26. The apparatus of claim 1 wherein the time-dependent response in the sample comprises at least two acoustic frequencies measurable simultaneously in the at least one signal beam.

27. The apparatus of claim 1 comprising a collimating lens, between the probe laser and the sample, for collimating the probe laser beam.

28. The method of claim 17 wherein the collecting overlaps the at least three beams in a cylinder-shaped volume having a long axis that increases with the focal length of the imaging system.

29. The method of claim 17 wherein a focus resulting from the method is significantly sharper than that from a similar method having only two sub-beams.

30. The method of claim 29 wherein the at least one signal beam is stronger than that of a similar apparatus having only two sub-beams.

31. The method of claim 17 wherein the time-dependent response in the sample comprises at least two acoustic frequencies measurable simultaneously in the at least one signal beam.

32. The apparatus of claim 17 comprising collimating the probe laser beam prior to the diffracting.

* * * * *